US011259743B2

(12) United States Patent
Obma et al.

(10) Patent No.: US 11,259,743 B2
(45) Date of Patent: Mar. 1, 2022

(54) METHOD FOR IDENTIFYING HUMAN JOINT CHARACTERISTICS

(71) Applicant: Strive Orthopedics, Inc., Green Bay, WI (US)

(72) Inventors: Padraic R. Obma, Green Bay, WI (US); Visnu D. Fraenkel, Madison, WI (US); Wayne M. Hansen, Lodi, WI (US)

(73) Assignee: Strive Orthopedics, Inc., Green Bay, WI (US)

( * ) Notice: Subject to any disclaimer, the term of this patent is extended or adjusted under 35 U.S.C. 154(b) by 394 days.

(21) Appl. No.: 15/916,017

(22) Filed: Mar. 8, 2018

(65) Prior Publication Data

US 2018/0256090 A1    Sep. 13, 2018

Related U.S. Application Data

(60) Provisional application No. 62/583,244, filed on Nov. 8, 2017, provisional application No. 62/468,558, filed
(Continued)

(51) Int. Cl.
*A61B 5/00*   (2006.01)
*A61B 5/107*   (2006.01)
(Continued)

(52) U.S. Cl.
CPC .......... *A61B 5/4528* (2013.01); *A61B 5/1079* (2013.01); *A61B 5/112* (2013.01);
(Continued)

(58) Field of Classification Search
CPC ..... A61B 5/4528; A61B 5/1079; A61B 5/112; A61B 5/1121; A61B 5/4504;
(Continued)

(56) References Cited

U.S. PATENT DOCUMENTS 5,316,547 A    5/1994 Gildersleeve
5,413,116 A    5/1995 Radke et al.
(Continued)

FOREIGN PATENT DOCUMENTS

AU    2007209792 A1    9/2007
AU    201421062 A1    3/2015
(Continued)

OTHER PUBLICATIONS

Malcolm J. Beynon, Lianne Jones, and Catherine A. Holt, Classification of Osteoarthritic and Normal Knee Function Using Three-Dimensional Motion Analysis and the Dempster-Shafer Theory of Evidence, IEEE Transactions on Systems, Man, and Cybernetics—Part A: Systems and Humans, vol. 36, No. 1, Jan. 2006, USA.

*Primary Examiner* — Daniel L Cerioni
*Assistant Examiner* — Deirdre M Willgohs
(74) *Attorney, Agent, or Firm* — Erin E. Kaprelian; Joseph S. Heino

(57) ABSTRACT

A method for identifying human joint characteristics, the method including the steps of: using a mobile imaging device, taking at least one image of the joint, and then identifying a joint pain location by identifying three different locations in the image near the joint, so that a center point between the locations can be triangulated.

4 Claims, 5 Drawing Sheets

Related U.S. Application Data on Mar. 8, 2017, provisional application No. 62/468,565, filed on Mar. 8, 2017.

(51) Int. Cl.
  *A61B 5/11* (2006.01)
  *G16H 30/40* (2018.01)
  *G16H 20/30* (2018.01)
  *G16H 10/65* (2018.01)
  *G16H 15/00* (2018.01)

(52) U.S. Cl.
  CPC .......... *A61B 5/1121* (2013.01); *A61B 5/4504* (2013.01); *A61B 5/4887* (2013.01); *A61B 5/6813* (2013.01); *A61B 5/6898* (2013.01); *G16H 20/30* (2018.01); *G16H 30/40* (2018.01); *A61B 2562/0219* (2013.01); *A61B 2562/0247* (2013.01); *G16H 10/65* (2018.01); *G16H 15/00* (2018.01)

(58) Field of Classification Search
  CPC ... A61B 5/4887; A61B 5/6813; A61B 5/6898; A61B 2562/0219; A61B 2562/0247; A61B 5/45; A61B 5/103; A61B 5/107; A61B 5/1072; A61B 5/1075; G16H 20/30; G16H 30/40; G16H 15/00; G16H 10/65
  USPC ....................................................... 600/595
  See application file for complete search history.

(56) References Cited

U.S. PATENT DOCUMENTS

| | | | |
|---|---|---|---|
| 5,415,625 A | 5/1995 | Cassford et al. | |
| 5,520,622 A | 5/1996 | Bastyr et al. | |
| 5,542,911 A | 8/1996 | Cassford et al. | |
| 5,546,955 A | 8/1996 | Wilk | |
| 5,577,089 A | 11/1996 | Mazess | |
| 5,611,353 A | 3/1997 | Dance et al. | |
| 5,833,608 A | 11/1998 | Acker | |
| 5,842,982 A | 12/1998 | Mannheimer | |
| 5,924,074 A | 7/1999 | Evans | |
| 5,961,474 A | 10/1999 | Reis | |
| 6,334,852 B1 | 1/2002 | Seyl | |
| 6,470,199 B1 | 10/2002 | Kopotic et al. | |
| 6,820,025 B2 | 11/2004 | Bachmann et al. | |
| 7,056,297 B2 | 6/2006 | Dohno et al. | |
| 7,097,459 B2 | 8/2006 | Ueda et al. | |
| 7,291,119 B1 | 11/2007 | de Guise et al. | |
| 7,433,726 B2 | 10/2008 | Perkins | |
| 7,481,780 B2 | 1/2009 | de Guise et al. | |
| 7,602,301 B1 | 10/2009 | Stirling et al. | |
| 7,627,451 B2 | 12/2009 | Vock et al. | |
| 7,825,815 B2 | 11/2010 | Shears et al. | |
| 7,947,082 B2 | 5/2011 | Guidera et al. | |
| 7,972,246 B2 | 7/2011 | Shinomiya et al. | |
| 8,045,180 B2 | 10/2011 | Friemel | |
| 8,109,890 B2 | 2/2012 | Kamiar et al. | |
| 8,133,181 B2 | 3/2012 | Yuk et al. | |
| 8,139,822 B2 | 3/2012 | Selner | |
| 8,167,954 B2 | 5/2012 | Despres, III et al. | |
| 8,206,325 B1 | 6/2012 | Najafi et al. | |
| 8,265,730 B2 | 9/2012 | Alexander et al. | |
| 8,715,208 B2 | 5/2014 | Hodgins et al. | |
| 8,753,275 B2 | 6/2014 | Najafi et al. | |
| 8,775,972 B2 | 7/2014 | Spiegel | |
| 8,941,392 B1 | 1/2015 | Reese | |
| 8,979,665 B1 | 3/2015 | Najafi et al. | |
| 9,005,141 B1 | 4/2015 | Najafi et al. | |
| 9,114,296 B2 | 8/2015 | Reynolds, III | |
| 9,161,840 B2 | 10/2015 | Hayes, Jr. et al. | |
| 9,198,821 B2 | 12/2015 | Unluhisarcikli et al. | |
| 9,222,764 B2 | 12/2015 | Reese | |
| 9,286,355 B2 | 3/2016 | De Guise et al. | |
| 9,311,789 B1 | 4/2016 | Gwin | |
| 9,408,584 B2 | 8/2016 | Major et al. | |
| 9,476,692 B2 | 10/2016 | Reese | |
| 9,532,732 B2 | 1/2017 | Mezghani et al. | |
| 2001/0032059 A1 | 10/2001 | Kelly, Jr. et al. | |
| 2004/0057176 A1 | 3/2004 | Dhawan et al. | |
| 2004/0167390 A1 | 8/2004 | Alexander et al. | |
| 2006/0111628 A1* | 5/2006 | Tsai .................... | A61B 5/4504 600/407 |
| 2006/0245627 A1 | 11/2006 | Nagamune | |
| 2007/0129776 A1 | 6/2007 | Robins et al. | |
| 2007/0260418 A1 | 11/2007 | Ladetto et al. | |
| 2008/0108912 A1 | 5/2008 | NodeLanglois | |
| 2009/0024065 A1 | 1/2009 | Einarsson | |
| 2009/0079576 A1 | 3/2009 | Yankelevitz | |
| 2010/0174189 A1 | 7/2010 | Abraham | |
| 2011/0213275 A1 | 9/2011 | Boos et al. | |
| 2012/0054165 A1 | 3/2012 | Brown | |
| 2013/0054130 A1 | 2/2013 | Ye et al. | |
| 2013/0110547 A1 | 5/2013 | Englund et al. | |
| 2013/0137943 A1 | 5/2013 | Pinto Rodrigues | |
| 2013/0185310 A1 | 7/2013 | De Guise et al. | |
| 2014/0192206 A1 | 7/2014 | Holz | |
| 2014/0213929 A1 | 7/2014 | Dunbar | |
| 2014/0243651 A1 | 8/2014 | Kim et al. | |
| 2014/0342329 A1 | 11/2014 | Debenedetto et al. | |
| 2014/0347392 A1 | 11/2014 | Odessky et al. | |
| 2015/0134088 A1 | 5/2015 | Romeo et al. | |
| 2015/0260516 A1 | 9/2015 | Davey et al. | |
| 2015/0327794 A1* | 11/2015 | Rahman ............... | A61B 5/0022 600/595 |
| 2016/0242646 A1 | 8/2016 | Obma et al. | |
| 2016/0270696 A1 | 9/2016 | Lang et al. | |
| 2016/0302721 A1 | 10/2016 | Wiedenhoefer et al. | |
| 2016/0310066 A1 | 10/2016 | Wiedenhoefer et al. | |
| 2016/0345858 A1* | 12/2016 | Tromberg ............ | A61B 5/1128 |
| 2017/0143303 A1 | 5/2017 | Chen et al. | |
| 2017/0265800 A1 | 9/2017 | Auchinleck et al. | |

FOREIGN PATENT DOCUMENTS

| | | |
|---|---|---|
| WO | 2008120215 A1 | 10/2008 |
| WO | 2009023937 A1 | 2/2009 |
| WO | 201012135 A1 | 10/2010 |
| WO | 2013033669 A1 | 3/2013 |
| WO | 2015070183 A1 | 5/2015 |
| WO | 2016154230 A1 | 9/2016 |
| WO | 2016190948 A1 | 12/2016 |

* cited by examiner

METHOD FOR IDENTIFYING HUMAN JOINT CHARACTERISTICS

BACKGROUND

Current orthopedic pre-surgery and post-surgery joint examinations, as well as follow up therapy and evaluation, involve a need for a patient to visit a facility where physicians and imaging equipment are located. The physician visit and the use of the imaging equipment increase the costs associated with joint procedures. What is needed, but not currently available, is a way for patients to get these examinations accomplished in their home environment, using equipment commonly already present in the home, or which can be purchased at relatively low cost. Further, there is a need to identify desired methods of remediation given the exam results.

SUMMARY

A platform is disclosed to allow patients and non-orthopedic medical providers (primary care physicians, personal assistants, nurse practitioners, physical therapists, athletic trainers, nurses, etc.) to have orthopedic specific knowledge and skills to diagnose and treat patient injuries and conditions. This changes patient access points in health care and develops an entirely new patient driven work flow though the health system.

Disclosed is a procedure for in home self-evaluation of a human joint and for diagnosis of joint ailments, the method including the steps of: placing an item, such as a sticker in the form of a sensor, with a known characteristic, near the joint; using a mobile imaging device, taking at least one joint image of the joint; and using the image and the known characteristic of the item to determine a joint characteristic of the joint.

Disclosed is a sensor of a U shape, resembling the shape of a bat's wings (forearm). The sensor is adapted to be placed on the skin adjacent a joint with the opening between the wings positioned to be closest to the joint.

Disclosed is a method of determining a human joint bone alignment, the method including the steps of attaching a sensor to the skin of a user near the joint, capturing an image of the sensor on the user, and then using the image and sensor characteristics to determine a bone centerline.

Disclosed is a pair of sensors adapted to be attached to skin near a joint, wherein one sensor is a master sensor housing a sensor unit, a power source, and a transmitter, and one sensor is a slave sensor spaced apart from and hard wired to the master sensor. The master sensor is separable from the slave sensor, and can be used as a physical activity monitor.

Disclosed is a method for in home therapy wherein a patient's therapy performance can be validated or encouraged by comparing their therapy exercises with a video representation of optimal performance for their unique physical therapy protocol. In practice, the patient views their own range of motion (ROM) exercise as compared to a theoretical optimum ROM video for a specific time line in their treatment protocol that has been selected by their practitioner. Sensor recorded ROM will automatically provide the patient with validation of identified exercise parameters or inform them of percentage of ROM goal achieved. The sensor data will also be analyzed to see if changes to the patient remediation are required.

The disclosed method also allows for the detection of joint alignment at the knee or knees, such as varus (bowed legs) and valgus (knock-knee) conditions.

DRAWINGS

DESCRIPTION OF PREFERRED EMBODIMENTS

"Near a joint" as used herein means either on or in the vicinity of a joint.

"Image" as used herein may mean a photo, video, a plurality of transmitters (sensors), and from x-rays or magnetic resonance imaging (MRI), unless otherwise indicated. And "Item" as used herein means a sticker, marker, sensor, transmitter, or some other item that can be observed in an image.

By definition, a "joint" is the site of the junction of two or more bones of the body having a primary function of providing motion and flexibility to the frame of the body. Further, most joints allow considerable motion, the most common type being "synovial joints" which have a complex internal structure composed of the ends of bones, ligaments, cartilage, the articular capsule, the synovial membrane and sometimes serous sacs, or bursa. For example, the knee joint is a compound joint, which is a type of synovial joint, between the femur, the patella and the tibia. The elbow joint is the synovial joint between the humerus, the ulna and the radius.

"Mobile device" as used herein means a device capable to being carried and operated with one hand.

"Mobile imaging device" as used herein means a mobile device that includes an image sensor, such as a camera, mobile phone, laptop or desktop cam.

"Demographics" as used herein means patient's age, height, weight, sex, race, and other ethnographic and physical characteristics, as well as other patient history.

Figure 3:
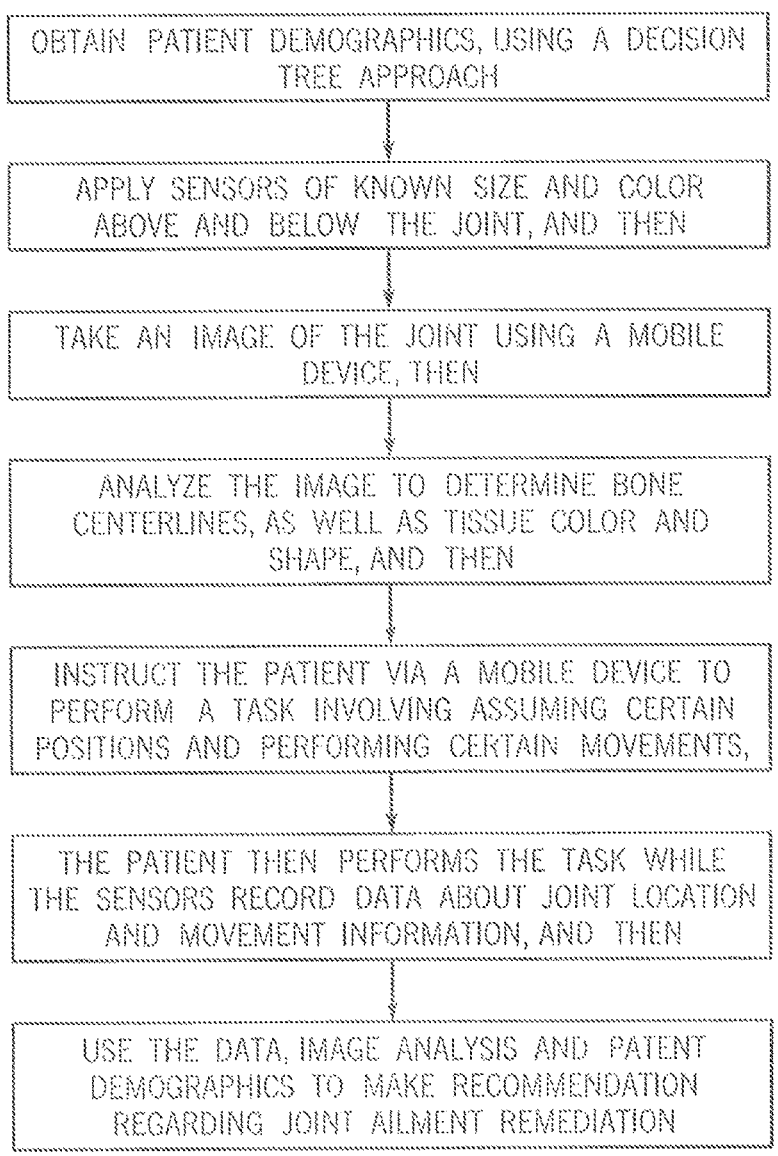
FIG. 3 is a flow diagram of a diagnosis procedure.

Disclosed herein is a method 80 of conducting a procedure for an in-home joint ailment diagnosis of a human joint (see FIG. 3), the method comprising a remediation recommendation method comprising the following steps of: obtaining patient demographics, applying sensors of known size and color above and below the joint, and then taking an image of the joint using a mobile device 12 (see FIG. 2). The remediation recommendation method then analyzes the image to determine bone centerlines, as well as tissue color and shape, and then instructs the patient via a mobile device to perform a task involving assuming certain positions and performing certain movements. The patient then performs the task while the sensors record data about joint location and movement information, and then the remediation recommendation method uses the data, image analysis and patent demographics to make a recommendation regarding joint ailment remediation.

More particularly, disclosed is a method of conducting a procedure for a diagnosis of a portion of a patient's human musculoskeletal system. The method comprises a remediation recommendation method comprising the steps of: obtaining patient demographics, applying sensors above and below at least one of the patient's musculoskeletal joints, and then taking an image of the patient's musculoskeletal joint using a mobile device.

The remediation recommendation method further comprises instructing someone to have the patient perform a task involving assuming certain joint positions and performing certain joint movements, then the patient performing the task while the sensors record data about the patient's musculoskeletal joint. And then next, using the task performance sensor data, an analysis of the shape of the patient's tissue around the patient's musculoskeletal joint in the image and the patient demographics to create a three dimensional representation of the bones in the joint and to make a recommendation regarding remediation.

More particularly, the image and sensor analysis serve to find the centerline of the bones around the joint in three dimensional space. This is more than just a two dimensional centerline. This is done by using the image capture, together with information about how the joint moves, and with tissue shape information. The tissue shape around the joint is important because some people have more or less flesh around a joint or limb and can have more of a cylinder, pear, triangular shape, etc., which needs to be taken into account, along with the sensor and other image data.

In one embodiment, the collecting the demographics and using the data, image analysis and patent demographics to make a recommendation regarding joint ailment remediation includes using a decision tree method.

In one embodiment, the remediation recommendation method does not include the step of a physician using the data, image analysis and patent demographics to make a recommendation regarding joint ailment remediation.

In one embodiment, the using the data, image analysis and patent demographics step does not including using any x-ray data.

In one embodiment, the taking of an image step includes the steps of: placing the joint within a camera field of view, and then, through software, recognizing the image, focusing, and then capturing the image.

In one embodiment, the method further includes the step of using the additional remediation wherein the remediation recommendation method to first make a recommendation regarding remediation further includes the step of using at least one of the sensors to monitor gait and other activity to make a further recommendation regarding remediation.

More particularly, the platform utilizes sensors placed on the patient's skin, a smartphone, tablet or laptop, photo capture, and patient questionnaires. The patient can also input any other data the patient may choose to share (such as x-rays, labs, MRIs, etc.) and instructions to patients or non-orthopedic providers on how to perform each step to establish a diagnosis. Once a firm diagnosis is made, treatment options (referrals, MRIs, medications, etc.) and prescriptions or orders can be made. This can be a self-contained system that takes the patient from an initial diagnosis to nonsurgical treatment, surgical recommendations and through any post-surgery care. The platform empowers patients and non-orthopedic providers with all existing technology to self-diagnose and then go through a variety of treatment plans.

This platform includes an initial exam, and the platform creates a flow through an entire episode of care. It can become a functional electronic health record that allows the patient to have input, transparency and some control. Machine learning empowers the system with data.

The initial exam is a remote exam that functions as an in person orthopedic surgeon exam. The initial intake form accumulates patient demographics (height, weight, age, painful joint, etc.). Patients can import previous health records or the platform can sync with other electronic health record platforms for that information. The platform takes a standing joint (hip, knee, shoulder, wrist, ankle, lumbar spine, cervical spine, etc.) photograph/video with the sensors in place. In one embodiment, the patient captures their own image. This image allows one to address joint alignment. And with the sensor position, one can measure circumference of the limb or torso, skin color. This allows the platform to make adjustments in calculations so the platform virtually places the sensors on the bone, instead of being several millimeters to centimeters off the bone on the skin. This makes the physical exam performed by the sensors much more accurate.

Once the patient has filled out the medical history, taken a joint image facilitated by the software and tablet/smartphone camera. The patient or provider is then instructed by the software to perform a physical exam with the sensors in place. In one embodiment, the photo is taken much like photo capture does for credit cards. When the joint is in the appropriate position, the camera captures the joint and takes measurements.

The exam consists of range of motion measurements (active and passive), ligament testing, strength testing, and a limb assessment for moles/swelling/skin color, etc. The patient also has the option of adding 1 or 2 or 3 pain sensors or locations where they are having pain and the platform can triangulate the pain sources. The platform empowers the patient or non-trained provider to do the same exam remotely as an orthopedic surgeon or neurosurgeon would do in person. The platform allows patients to input previous reports on x-ray, MRI, labs, surgery findings, etc. that also help adjust algorithms. This creates an interactive electronic health record that the patient can actively participate in and has autonomy over. The platform incorporating patient driven exams, input, etc. allows one to make a dynamic electronic health record that evolves over time with more data to make adjustments, better recommendations for prevention and intervention of musculoskeletal conditions.

In one embodiment, the step of identifying a location near a joint is in the form of selecting a location on a visual display of the image. In one embodiment, the step of identifying a location near a joint includes identifying three locations at three different locations near the joint so that a center point between the locations can be triangulated. The center point can then be regarded as the pain center, and knowledge of the pain center can be used with pain treatment.

In one embodiment, the step of using a handheld device to take at least one joint image of the joint comprises the step of placing at least two locating transmitters at different locations near a joint, with each transmitter communicating with the handheld device to identify their relative locations.

When the platform has accumulated all existing data the software creates a very precise diagnosis. The precise diagnosis allows the platform to generate a comprehensive treatment plan including referrals to surgeons, prescribe medication, digital health solutions (like weight loss platform, diet recs, mental health, etc.), physical therapy, and prescribe/order/send bracing, prescribe/schedule MRI's/Xrays/labs, etc. Essentially, anything that is done in a current clinical setting can be done on the platform. The diagnosis and treatment plan are nearly as accurate as an in person exam. A medical provider can monitor dashboards on the back end if necessary. To emphasize, the platform is intended to be either patient driven or non-specialist driven. The platform empowers people with fellowship trained knowledge, skill and expertise. The more the patient interacts with this dynamic platform the more accurate and precise it becomes.

The platform provides for follow-up exams as well. It is common for an orthopedic physician to assess someone in clinic, diagnose them and recommend certain interventions and follow-up in 6 weeks. The platform can monitor compliance of interventions remotely as long as the platform keeps them engaged in the software and then do follow-ups. If a patient is supposed to do 6 weeks of physical therapy before they get an MRI, the platform can monitor the data so it can be known if the patient qualifies for an MRI, or not.

A few examples follow of how the diagnostic works from real patient experiences in clinic. The platform can accurately diagnose between a knee meniscus (cartilage) tear and arthritis. This allows the platform to order an MRI (for a tear) or recommend arthritis treatment options (physical therapy, meds, injection, etc.). The difference is a significant savings in cost and reduction in surgical procedures. The platform can diagnose and differentiate between ACL tears (MRI and surgery) vs knee cap instability (bracing, medications, PT). It takes every single component of the self-administered history and physical exam to differentiate between these entities but the platform can and adjust recommendations based on this.

The platform data is also used to predict the future risk of certain injuries or conditions and make preventative recommendations as well. The platform can assess the future ACL tear risk of athletes and prescribe preventative exercises, bracing, or training adjustments. The platform can accurately predict the risk of a 40-year-old with knee pain developing arthritis and/or give a timeline on expectations until the joint will wear out and require joint replacement surgery.

The diagnostic platform then links to the pre and post-surgery episode of care platform which includes several remediation modules, such as sensor based physical therapy, diet, medication education, etc.

The platform can also be used if the patient has already been evaluated and gone thru a nonsurgical process either with the platform or by the traditional health care provider sequence, the decision for surgery (any orthopedic surgery . . . hip/knee replacement, lumbar/cervical fusions, knee arthroscopy, rotator cuff repair, etc.) having been made, or if the patient is on the path to surgery.

In one embodiment, the platform is deployed weeks to months ahead of a surgery to facilitate the best possible surgical outcome. The patient downloads the platform software to a smartphone/tablet and receives the sensors. The patient is then directed through an initial diagnostic exam and assessment with features described above including medical records input, x-ray/MRI/CT scans, labs, and patient demographics. The patient then applies the sensors and takes a joint photograph/video, does the initial self-administered sensor physical exam, activity tracker data, pain assessment, outcome measures, etc. All of this data is used to create a pre-surgical therapy, mental health, physical health, diet, etc. routine to optimize surgical results. The patient engages daily with the software/sensor platform to perform the routine things recommended. This can be for 1 week to 6 months ahead of surgery. Education about the surgery, process, providers, etc. also occurs.

The pre-surgical data is analyzed to determine optimal length of stay (outpatient, 1-4 night hospitalization), pain control strategy, physical therapy strategy (in home, self-administered, outpatient), predicts the length of the surgical implant (if doing joint replacement), and can be used to adjust computer software for robot assisted surgery.

In one embodiment, the post-surgery portion is similarly performed with the sensors, daily joint/limb/torso images (to monitor wounds, skin color, swelling, surgical site infections, blood clots, etc.) daily education components, digital health prescriptions (mental health, weight loss, diet), daily physical therapy monitoring, daily activity tracking (with the modular sensor or with the aid of another patent activity tracker), pain control and medication use, etc. This is self-contained in that the platform can handle a variety of healthcare related issues, such as medication refills, appointments for provider/therapy, and further home monitoring.

All existing data is analyzed and used to adjust the post-surgery protocols. For example, if a patient isn't getting good pain control, medications can be adjusted and monitored. If remote physical therapy is going well, existing outpatient visits can be avoided (saving money) or conversely, if home rehab isn't going well, more appointments can be made. If photo capture picks up signs of infection, antibiotics can be prescribed and appointments made.

The platform is initially focused on a 4-month episode of care: 1-month pre-surgery through 3 months post-surgery. This is ideal for joint replacements but can be adjusted for other surgical procedures.

All of this data from the diagnostic through a full surgical recover is analyzed and creates more advanced and accurate software and treatment paths in the future.

Figures 7, 8:
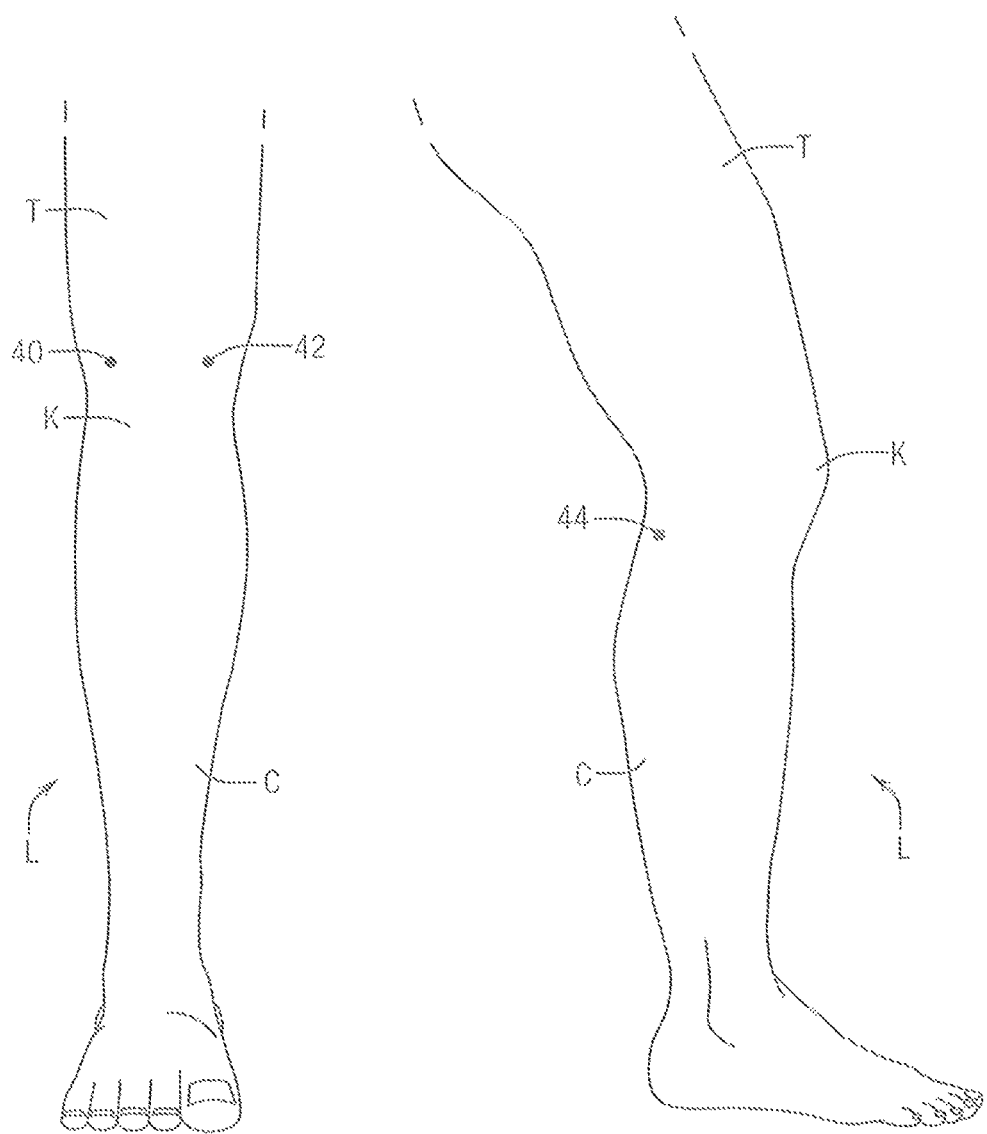
FIG. 7 illustrates a front image of a human leg with an indication of pain locations.
FIG. 8 illustrates a right side image of the human leg of FIG. 7.

In one embodiment, in addition to the pair of sensors above and below a joint or group of joints, the platform allows patients to place additional pain sensors or to otherwise identify locations at their source of pain (see pain locations 40, 42 and 44 in FIGS. 7 and 8). These additional sensors act like homing beacons that talk with the pair of sensors and allow one to triangulate the pain source. For example, if the patient places a pain sensor at the level of their navel and the platform is doing a back exam with the pair of sensors, the platform can triangulate the pain to a certain lumbar spine level. Further, if a pain sensor for a back exam is placed by the big toe, this signals that there is actually a pinched nerve at Lumbar level 5.

Photo capture with sensors in place gives a reference point of a known object's size, shape and color to monitor limb or torso circumference changes, skin color changes, to monitor for infection or blood clots. Photo capture and video capture with sensors in place also provides data to adjust software to virtually place sensors on the bone, not just on the skin. In one embodiment, each of the sensors has vertical lines 22 of a color different than the remainder of the sensor to aid the use of the image to analyze the joint. Photo capture combined with patient height, weight and age gives one the ability to calculate where the sensor would be on the bone so the platform can get rid of several centimeters of excess tissue that can give false readings. Video capture with sensors on allows one to see what micro motion or macro motion is being generated by the soft tissue and subtract out the motion to make more accurate measurements.

The platform uses the photo capture data (alignment, circumference, etc.), range of motion and alignment data from sensors and information from intake form (decision tree) to make a remediation recommendation. The platform can then generate a very accurate depiction of what the joint would look like in an X-ray. The photo capture and sensor data help one determine degree of varus/valgus. Sensor motion data is good at predicting if there are knee bone spurs and where (for example, lack of extension indicates knee cap spurs, loss of flexion to less than 100 degrees indicates there are posterior bone spurs), and patient reported data (such as body mass index) give the platform insight into stresses placed on the knee. This allows the platform to generate a very accurate virtual X-ray. The platform can also use skin temperature information to generate a heat map of where stresses are on the knee at any given range of motion utilizing this data.

In the disclosed method, a decision tree method is used by the platform to provide a method for diagnosing knee injuries by asking the patient to answer a series of multiple-choice questions. As each question is answered, a list of possible diagnoses along with their probability is built. The results are presented as a ranked list. The questions and possible diagnoses are compiled based on actual patient interviews conducted at orthopedic clinics. Over time, this method can be further enhanced, based on user experience with the platform, using, for example, machine learning and artificial intelligence techniques.

Results are hidden from all parties until the final diagnosis is produced. Additionally, the doctor may keep the results hidden until he or she has had a chance to input a manual diagnosis. A database stores both the results of the decision tree method exam and the actual answers to each question. Based on actual medical results the diagnoses probabilities are updated through either algorithmic or manual methods.

Each answer provided within the questionnaire adds or removes the probability of one or more of several possible results. Data from the knee position sensor adds or removes probability one or more of several possible results. Probabilities are computed from a database that hosts professional insights and/or actual outcomes. Probabilities for each question are automatically, or manually updated as new information is added to the database from new exams performed.

The questionnaire is dynamic. Some questions may be skipped or added based on previous answers to questions. A patient can use the decision tree method on multiple occasions over a period of time, providing a history that can be used to show the patient's progress or regression. And exams can be performed with or without the assistance of medical staff.

It is important to note that the same decision tree method principles are used for pre and post-surgery monitoring. The platform takes all these data points and monitor for complications, failure to progress in home therapy, mental health changes, narcotic usage, etc. The questions are changed, the photos and sensor data is different for the algorithm input, but it is all in the same platform.

The motion sensor is used in conjunction with software to create sensor enhanced exams. These exams measure the patient's range of motion, knee bend angle, and other factors in a way that is reproducible and can be done remotely without a doctor's supervision, if necessary. The patient attaches motion sensors to their injured leg by placing one sensor above and one below the knee. The sensors attach using a disposable/replaceable adhesive pad.

The patient or doctor chooses one of three exams: Knee Bend/Extension, Varus/Valgus, or Toe Push/Pull. It is important to note that there may be additional exercises. Also, a therapy platform can have a more robust list of exercises than the 3 listed. The patient assumes a starting position as indicated by the software, and moves their leg as indicated for the chosen exam. Typically, 3 or 4 repetitions are requested. As the exam proceeds, the software collects data points from the sensor which are translated into orthopedic measurements. These measurements contribute to the software that ultimately produce a diagnosis or key information regarding the patient's conditions.

During the exam, the software displays a model of the patient's knee that moves in real time according to the patient's actual movements. This helps guide the patient to make the correct movements for the exam, and provides important visual and/or audible or other forms of sensory feedback. A real-time graph of the generated orthopedic measurements can also be shown.

Previous efforts show relative range of motion, that is to say, degrees of movement, but without a reference to starting position. With the addition of a calibration step to a known 90 degree or 0-degree reference, the disclosed method can generate actual range of motion referenced to an absolute versus a relative value. This is critical for the range of motion values to be of maximum value to a physical therapist.

An infrared sensor, or the visual image, or both, can be used to measure temperature. Further, a resistive temperature device built into the sensors can be used to measure temperature. Height measurements can be derived from barometric pressure sensors within the sensors. And the sensors above and below a joint or group of joints should be described as 'up to 10-axis' sensors.

In one pre and post-surgery self-evaluation method, a sensor on the thigh incorporates electromyography technology to monitor muscle firing or lack thereof. EMG sensors can be applied to other muscle groups as well for different joints/group of joint monitoring (lumbar spine muscles and/or abdominal muscles for low back conditions, neck and deltoid muscles for shoulder conditions, etc.

Data from the sensor exams is stored in both detail and aggregate form, allowing for later analysis and historical reporting.

Sensor exam results are combined with the decision tree results to produce a more accurate diagnosis. This is done by either eliminating or re-enforcing the decision tree method's results according to how well the user performed the exercises. One of the current limitations with virtual care, remote care and telemedicine is the inability to perform a physical exam. The sensor technology enables a physical exam remotely not requiring a provider to 'lay hands on' a patient to get true physical exam data.

The disclosed method also provides a visual record of the patient's legs and a way for the doctor to estimate the patient's degree of varus or valgus deformation without direct access to the patient. To do this, the patient is asked to indicate which leg has the injury (left, right, or both).

Then the patient is directed to take a picture of his or her legs. A visual guide and example pictures are shown to help direct the patient to take a picture from the right distance and angle. In addition to knee angles (Range of Motion), it is important to measure joint laxity, translation, rotation, elevation changes, etc.

In one embodiment, the patient is asked to photograph their legs while standing in front of a plain background of a known color, such as a green screen. In other embodiments, not green screen is needed.

Figures 5, 6:
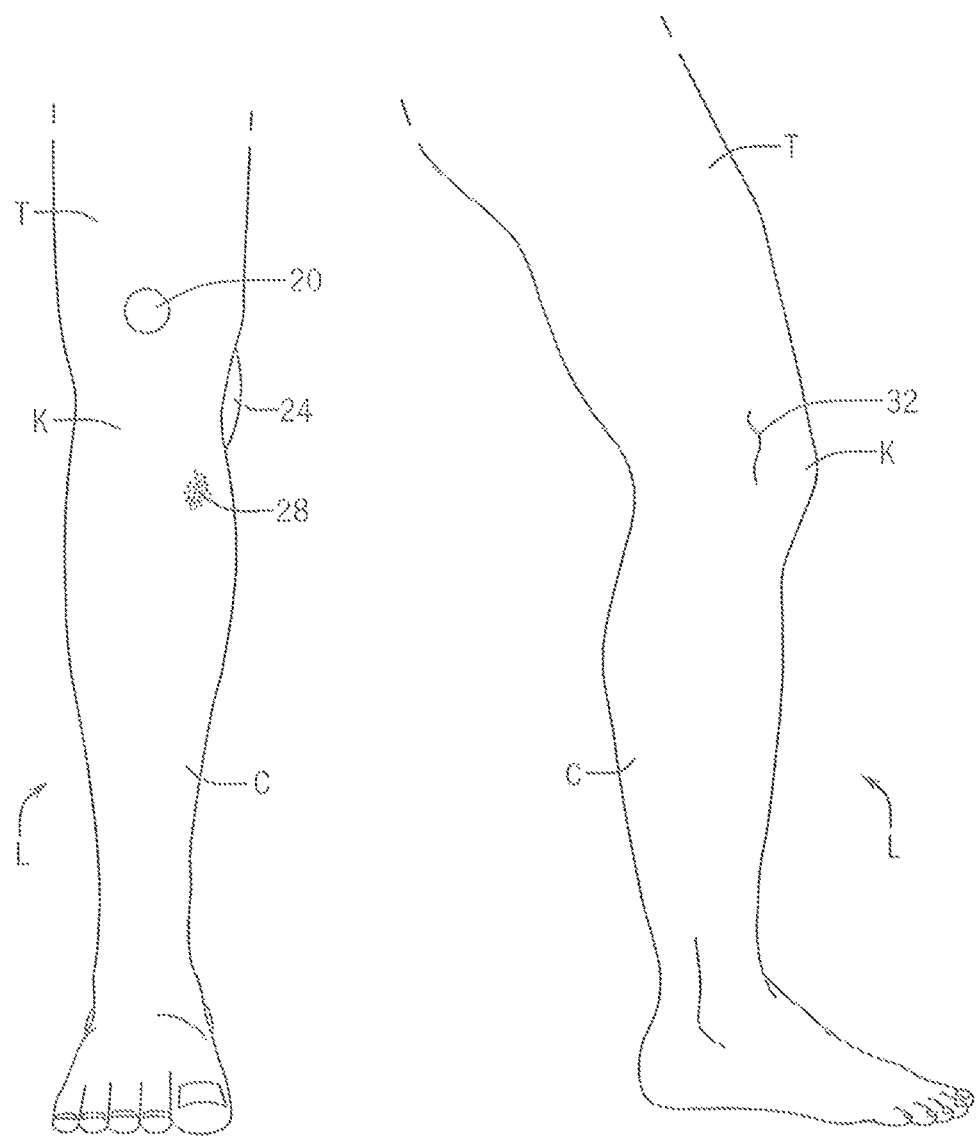
FIG. 5 illustrates a front image of a human leg with a sticker and leg ailments.
FIG. 6 illustrates a right side image of the human leg of FIG. 5.

The software can then provide the following information by analyzing the photograph: Height: based on the size of the sensors as seen in the photograph, can be used to estimate the patient's height and also their distance from the camera when the photo was taken. Knee Angle: the patient's varus or valgus deformation can be measured by detecting the relative positions of three stickers 20 (only one is shown in FIG. 5). Shin and thigh circumference: the software can make these measurements by observing the contrast between the patient's leg and the known background color at various locations in the photograph. Swelling: the software can detect swelling 24 (see FIG. 5) by checking for abnormal variations in the shape or size of the leg by using photographic pixel count. Discoloration: the platform can compute the patient's average skin tone and note areas that vary significantly from the average due to discoloration 28 (see FIG. 5), especially around an incision 32 (see FIG. 6). The image is color-corrected based on the known colors of the sensors.

In one embodiment, the platform compares its measurements to normal values for a patient of similar demographics and automatically flag potentially abnormal conditions. And in some embodiments, the platform also provides instructions and tools for allowing users to interact with the platform to improve measurements.

In one embodiment, a doctor can later view the picture on a screen that provides three moveable pinpoints. The doctor is directed to arrange the pinpoints over the injured leg in a fashion that puts the midpoint directly over the patient's patella, the upper point centered on the femur, and the lower point centered on the tibia. Using the three points, the software computes and stores the angle of varus or valgus seen in the photograph. The doctor may also input the knee angle manually if it is determined that the photograph is unsuitable for automatic estimation. In addition to knee angles (Range of Motion), it is important that to measure joint laxity, translation, rotation, elevation changes, etc.

As a part of the disclosed method, the platform can also use automated photographic analysis to measure and record various conditions related to orthopedic injury. In one method the patient is asked to place three small stickers or sensors on each leg in the following positions: centered on the patella, centered on the femur, and centered on the tibia. The ideal situation with this is the sensors above and below the joint serve as the 2 primary stickers. Adding a pain sensor over the patella as a third sticker or even additional stickers, can be used. Instead of a sticker, a patient can hold a "sensor on a stick" to locate pain, or touch or click on an image of the joint to indicate a pain location.

The disclosed method can also include microphones on the skin (similar to a conventional throat microphone) to listen to joint sounds. Using the microphone to add an audio recording to the analyzed data, permits the method algorithm to determine if there is a lot of crunching/cracking of the knee cap. If present, this could indicate a pre-arthritic knee cap condition called chondromalacia patella.

The platform also allows the patient to assist in customizing their joint replacement surgery or other types of surgery. This includes the patient answering extensive questionnaire (activity levels, goals in life, goals after surgery, BMI, etc.), followed by using the sensors for an initial joint evaluation including gait analysis, and using activity tracking data. The patient is then helping to customize their surgery. This allows the platform to determine the optimal type of implant, the optimal implant positions, the optimal recovery process, etc. It is a patient driven platform to create customized surgeries using the technology.

The platform provides sensors that are modular and allow the master sensor to clip into a wrist band so it doubles as an activity tracker.

Figures 1, 2:
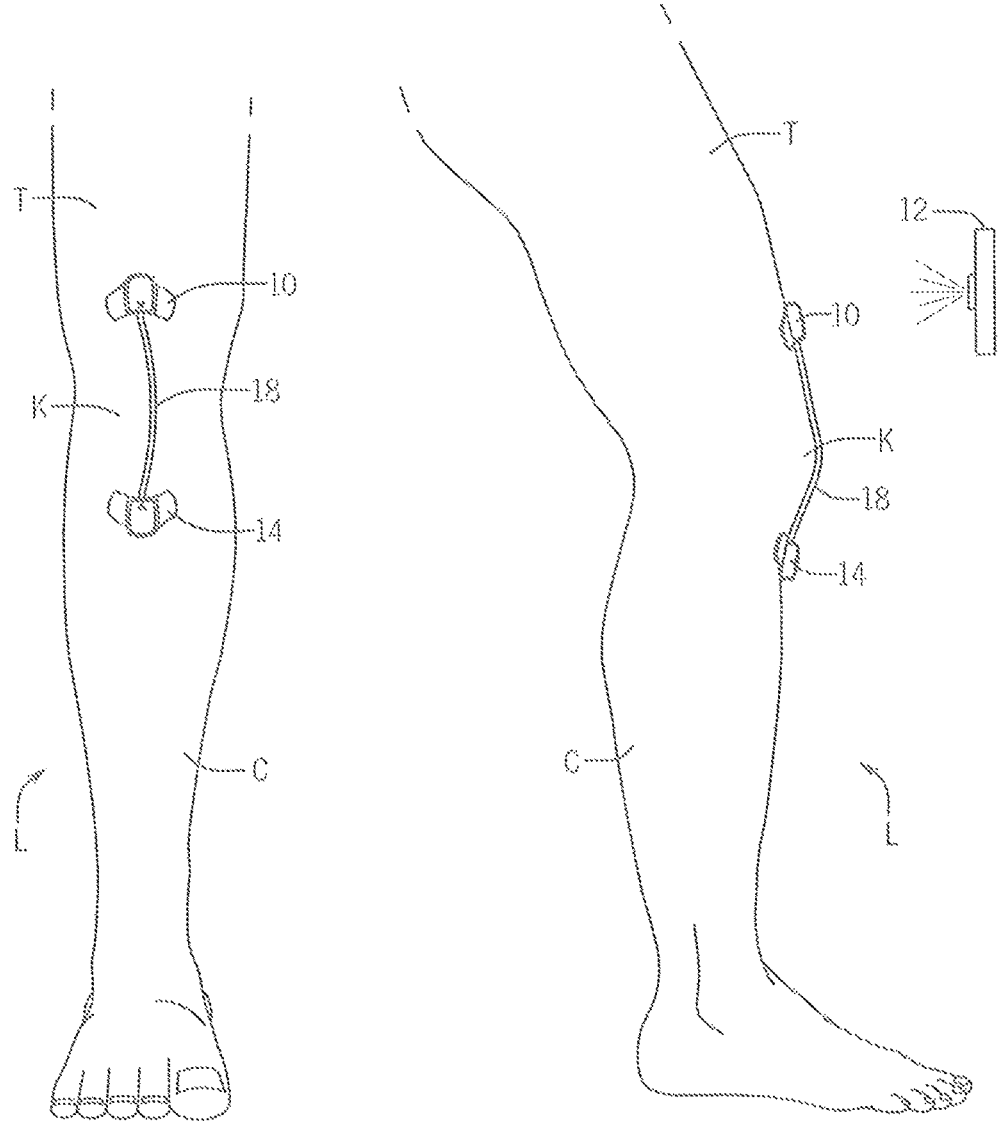
FIG. 1 illustrates a front image of a human leg with sensors according to this disclosure disposed above and below a knee.
FIG. 2 illustrates a right side image of the human leg of FIG. 1.
Figure 4:
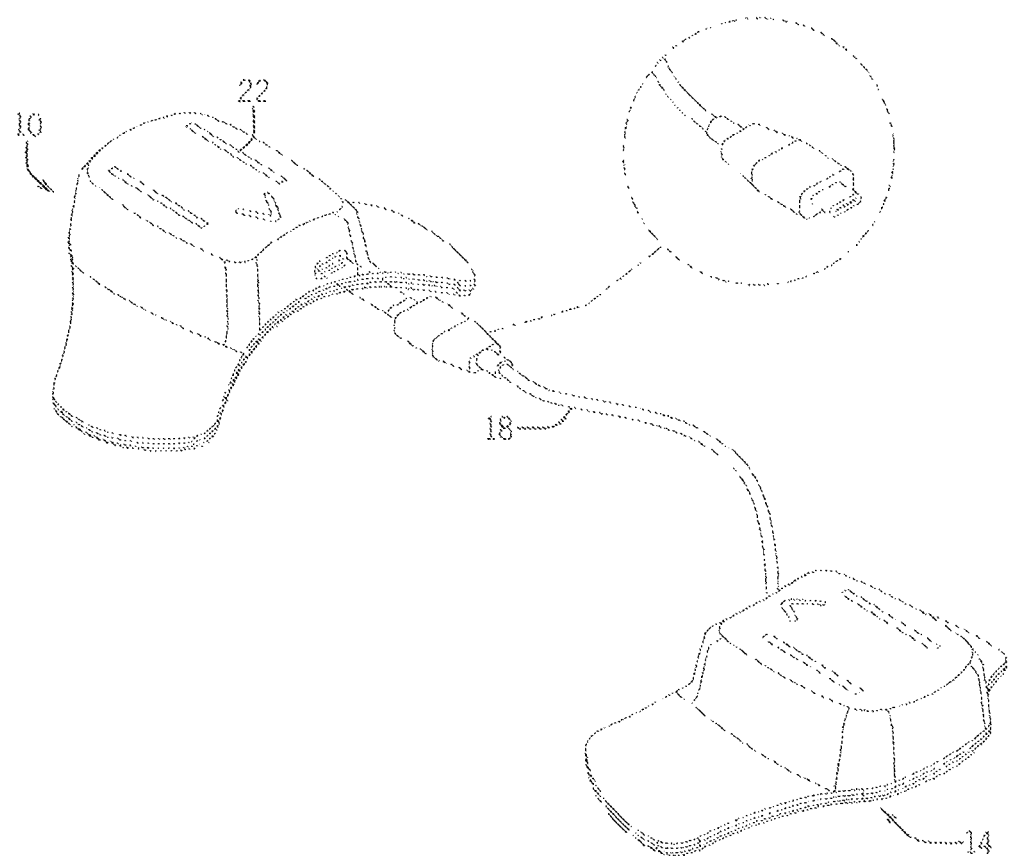
FIG. 4 is a top perspective view of the pair of sensors shown in FIG. 1, with an exploded view of a connector.

Disclosed in FIGS. 1, 2 and 4 is a pair of sensors 10 and 14 for attachment to the skin of a user. Each sensor is of a predetermined size, shape and color. As a result, a user can use a camera to take a picture of the sensor on the skin. Because of the sensor's known characteristics, observations can be made about the user. For example, if a sensor is attached to the skin adjacent the user's knee, as shown in FIG. 1, the width of the tissue around the knee (the thigh and shin circumferences) can be determined. The coloring of the tissue around the knee can also be observed in order to see if there are any problems with swelling or infection, for example. More particularly, the pair of sensors 10 and 14 adapted to be attached to skin near a joint K. The master sensor 10 is separable from the slave sensor 14, and can be used as a physical activity monitor.

More particularly, each of the disclosed sensors is of a U shape, resembling the shape of a bat's wings (forearms), as shown in FIGS. 1 and 4. It has been determined that this shape is ideal for both adhering to and continuing to adhere the sensor to a user's skin. This shape also provides a comfortable experience for the user. The sensor is placed on the skin adjacent the knee with the opening between the wings positioned to be closest to the knee cap.

The width of the tissue around the knee, together with user information, especially the age and gender of the user, and information about the patient's activity level, can be used to accurately determine the likely centerline of the bones around the knee.

More particularly, the use of image data (pixels, relative size to sensor size, etc.) to measure thigh and shin circumference provides bone centerline information. The determination of bone centerlines is important when it comes to accurately tracking the knee joint metrics. The bone centerline information comes from tissue thickness calculations, as well as typical bone size given the patient's age and gender, and the patient's particular activity level.

The platform will also have patients do exercise (walk, run, etc.) with the sensors on. For example, if a patient's gait with the sensors indicates they have a lateral thrust in the gait, the platform can adjust computer and robotic navigation algorithms to account for this with adjusting implant positions, ligament balancing or bone cuts. If the sensors pick up a PCL tear, the platform use a Posterior Stabilized knee implant rather than a Cruciate Retaining implant. The platform can generate with the heat map exactly where the increased stresses will be on a knee after the replacement which will help one to adjust implant positions or choose different implants or implant materials to account for the additional stresses.

Having the bone centerline information has a number of benefits. The centerline data can be used to diagnose leg problems. The bone centerline information can also be used to aid in treatment of the knee. In particular, robotic assistance in knee replacement is now being done. For example, one such robotic-arm assisted surgery machine is manufactured by Stryker. To aid the surgeon during a knee replacement using the Stryker machine, position transmitters are screwed into the bones on either side of the joint. Using the sensors disclosed herein, the bone centerline information can be provided to the robotic assistance machine without the need to use position transmitters screwed into the bones, or in addition thereto, in order to improve information available to the Stryker machines software to aid the surgeon.

With the aid of the disclosed sensors, one can obtain pre and post-surgical data which can be combined with machine learning to create better joint replacement surgery with robotics, and better software for joint positioning, alignment etc. One can also determine how long a joint replacement will last and ways to improve the operations to make the joint replacement feel like a normal knee and improve the longevity of the implant.

In other words, the sensor, patient data and image capture can be used not only to determine the bone "centerline", but also joint alignment. The sensor data, photo capture data and patient data are used to create software to "place the sensor on the bone" much like if it were directly adhered to the bone. This provides the most accurate data. The calculations of the sensor on the bone come from all the data that is collected.

The information provided by the sensors when applied to the users skin can provide user information both pre-surgery and post-surgery. For example, the sensors can be used about 20 minutes a day, five days a week, for about one month before surgery and three months after surgery. In addition to checking the knee, the sensor can also, on occasion, once or twice a week, be used as an activity monitor, with the sensor on the wrist or some other appropriate location.

The disclosed sensor is intended to be adhered to the user's skin for a number of 20 minute periods. In order to facilitate the repeated adherence of the sensor to the skin, a reusable and replacement gel pad is releasably fastened to the back of the sensor and to the user's skin.

In the disclosed embodiments, the pair of sensors comprise the master sensor 10 and the slave sensor 14. The master sensor, shown above the knee in FIG. 1, houses the disclosed sensor unit, as well as a power source, such as a battery, and a transmitter, such as a wireless transmitter. The slave sensor 14 is hard wired via wire 18 to the master sensor, in order to both utilize the master sensor's power source, and to rapidly transmit data from the slave sensor unit to the master sensor. A central processing unit in the master sensor processes data from the sensor units before it is transmitted to a handheld device for further data transmission, analysis, and the saving of the data.

The disclosed pair of sensors have a single power source located in the master sensor. In other embodiments, both sensors can be powered. Using the location information from each of the sensing units incorporated it into each of the sensors, bone centerline location information can be transmitted to a receiver. When the receiver is attached to the robotic assistance device, bone centerline information will be available to the robotic assistance device software to aid in the operation of the robotic device, as described above.

In the embodiment of FIG. 1, the master sensor 10 shown is intended to be hard wired to the slave sensor 14, and the pair of sensors 10 and 14 can be separated from one another. To aid in this separation, a standard power connector is used to attach the cable 18 to the master sensor (such as a USB-C connector, a 24-pin USB connector system allowing transport of data and power). Once separated, the master sensor 10 can be used without the slave sensor 14. For example, the master sensor 10 can be applied to a user's wrist (not shown), and operated like an activity sensor. This allows for the diagnostic system to be used not only for knee evaluation, but also for activity monitoring.

The sensor in accordance with the present disclosure utilizes a gyrometer for measuring limb joint rotation and an accelerometer to measure speed and directional changes in limbs or limb parts. More specifically, certain applied algorithmic steps are used to accomplish these measurements. The algorithmic steps in accordance with the present disclosure utilize applied "quaternion" matrix mathematics, which are used to determine a rotation angle and the vectored direction of a rotation. Quaternions are used in particular for calculations involving three-dimensional rotation, and describing spatial rotations in particular, and are more compact and quicker to compute than are representations by other vector matrices. As applied to the present disclosure, the accelerometer provides the amplitude of force in terms of "G-forces" (with "G" from the word "gravitational"), G-force being a measurement of the type of acceleration that causes weight. Viewed another way, physical parameters that are analyzed according to this aspect of the present disclosure include a "mass" in "motion"—the "mass" being a limb or Limb part—as G-force can also be described as a "weight per unit mass". The term "motion" can encompass rotation, reciprocation, oscillation, gyration, combinations thereof, or any other continuous, alternating, periodic, repetitive and/or intermittent change to the location or arrangement of the limb or limb part.

In the quaternion math matrix concept mentioned above, a magnetometer is also necessarily incorporated to measure directional orientation of the patient, the patient's limb or a limb part—the magnetometer providing a fixed point for the sensor in 3-dimensional space. This is an important addition as the magnetometer provides a fixed point in space that can be used to determine the spatial relationship between any two sensors. In the wearable sensing devices of the present disclosure, the magnetometer in a first wearable sensing device provides a point for initial calibration, or the point of start for positional changes to be detected, which essentially serves as a compass in the dueling sensor concept disclosed and claimed herein. In short, the magnetometer gives the gyrometer and accelerometer combination fixed points to calibrate from. Without the magnetometer, the only parameter that can be established is the distance between any two of the sensors, which is dynamically variable in almost all instances—one example being where one sensor is located above a joint and one is located below the joint. Upon continuous flexing of the joint, the distance between the two sensors is likewise continuously changing as is the relative rotation of the one sensor based on its orientation in relation to the other.

Each sensor preferably uses low energy digital technology and BlueTooth®, iBeacon™ or other short-wavelength ultra-high frequency (or "UHF") radio wave technology in the industrial, scientific and medical (or "ISM") band ranging from 2.4 to 2.485 GHz (BLUETOOTH is a registered certification mark of Bluetooth Sig, Inc. and IBEACON is a trademark of Apple Inc.); radio frequency ("RF" and "RFID") technology; and/or other electronic data messaging modalities to send the monitored data to a receiver, a personal computing device, a smartphone, a terminal (as defined below) or to an electronic medical record ("EMR") for the user patient.

A microelectromechanical systems configuration for the master sensor comprises an on-board power supply, a microprocessor, a local memory (which can also be transitory or non-transitory memory), six or ten axes sensing elements (plus others, as required) and a transceiver having at least one wireless antenna, all contained within a single housing.

The controller, or microprocessor controls the overall operations of the sensor and its associated electronics. For example, the microprocessor performs the control and processing associated with the monitored parameters.

In one method of using the disclosed sensors, a handheld device is used to take at least one joint image of the joint includes an image at one angle relative to the front surface of the joint and another image at another angle relative to the front surface of the joint.

In one embodiment, the joint is a knee. And in another embodiment, the joint is between vertebrae in the cervical spine. In still other embodiments, the disclosed methods can be applied to any human joint or group of joints.

In one embodiment, the step of using a handheld device to take at least one joint image of the joint comprises the step of placing at least two sensors at different locations near a joint, with each sensor communicating with the handheld device to identify their relative locations.

Referring more particularly to FIG. 1, the patient's leg L is shown to comprise a thigh T, knee K and calf C. The sensors are disposed along the user's femur and disposed along the user's tibia. More particularly, items can be disposed on the ventral portion or front of the leg L, to the dorsal portion or back of the leg L or even at a point to the inside of the leg L.

Measured parameters can include range of motion (flexion/extension), where a loss of motion may predict arthritis or cartilage damage; joint rotation, where excessive rotation may increase the risk of cartilage tears; joint alignment (varus/valgus), where increasing varus or valgus is another indicator of arthritis in the joint; ligament laxity, where excessive translation of the tibia indicates the tear of an anterior cruciate ligament ("ACL"), an excessive tibia and femur gap on the inner (medial) or outer (lateral) joint line can indicate tearing of the medial collateral ligament ("MCL") or the lateral collateral ligament ("LCL"), or how well a ligament surgery was done; time spent with knee flexed more than 90°, with more time indicating increased risk of knee cap pain; number of times the knee is flexed more than 90°, which can indicate the risk of knee cap pain; and number of times the knee is cycled per day (i.e., going from flexion to extension and back), which can be used to predict survival time in years of knee replacement.

The invention claimed is:

1. A method for identifying human joint characteristics, comprising:
    attaching a pair of sensors to skin surrounding a joint of a user, wherein:
        a first sensor is attached to skin above the joint; and
        a second sensor is attached to skin below the joint;
    capturing an image of the joint, wherein the captured image includes the joint and the pair of sensors;
    capturing a plurality of measurements of the joint, wherein capturing a plurality of measurements further comprises:
        performing a series of exercises, wherein the exercises include a plurality of movements;
        recording the plurality of movements at the pair of sensors; and
        transmitting the recorded plurality of movements to a software platform;
    identifying a pain source, wherein identifying the pain source further comprises:
        placing at least one pain sensor at a location where the user is experiencing pain;
        transmitting the location of the at least one pain sensor to the software platform; and
        determining, based on the location of the pain sensor, the pain source;
    virtually placing the pair of sensors onto a bone of the joint, wherein the virtual placement of the sensors onto the bone of the joint is adjusted based on the captured image of the joint and plurality of measurements of the joint; and
    determining, based on the captured image of the joint and the captured plurality of measurements of the joint, a bone centerline of the joint, wherein determining a bone centerline of the joint further comprises:
        determining a width of tissue around the joint;
        determining a shape of tissue around the joint;
        determining an alignment of the joint; and
        determining the bone centerline based on determined width of the tissue, the determined shape of the tissue, and the determined alignment of the joint.

2. The method of claim 1, wherein capturing an image of the joint further comprises:
    capturing a first image relative to a front of the joint;
    capturing a second image relative to an angle of the joint; and
    integrating, by the software platform, the first image and the second image into a compound image of the joint.

3. The method of claim 1, wherein identifying a pain source further comprises:
    placing a plurality of pain sensors such that the plurality of pain sensors surrounds the pain location;
    capturing an image of the joint including the plurality of pain sensors;
    transmitting the captured image to the software platform; and
    triangulating the pain source based on the locations of the plurality of pain sensors.

4. The method of claim 3, further comprising:
    determining a location of the pair of sensors; and
    triangulating pain source based on the location of the sensors.

* * * * *